United States Patent
Spadaro et al.

Patent Number: 6,001,655
Date of Patent: Dec. 14, 1999

[54] METHOD AND SYSTEM FOR ESTIMATING THE TENDERNESS OF A MEAT PRODUCT

[75] Inventors: Maria Victoria Spadaro, Dallas; Rosana G. Moreira, College Station; Jimmy T. Keeton, College Station; David H. Allen, College Station, all of Tex.

[73] Assignee: The Texas A&M University System, College Station, Tex.

[21] Appl. No.: 08/881,675

[22] Filed: Jun. 24, 1997

Related U.S. Application Data

[60] Provisional application No. 60/020,715, Jun. 25, 1996.

[51] Int. Cl.$^6$ .......................... G01N 33/02; G01N 33/12
[52] U.S. Cl. ................... 436/21; 436/20; 73/760; 73/866; 426/231; 426/574
[58] Field of Search ..................... 436/20, 21, 174; 422/68.1; 426/231, 574; 73/78, 760, 790, 866

[56] References Cited

U.S. PATENT DOCUMENTS

| | | | |
|---|---|---|---|
| 3,593,572 | 7/1971 | Hansen | 73/81 |
| 3,732,727 | 5/1973 | Hinnergardt et al. | 73/81 |
| 3,956,924 | 5/1976 | Hansen et al. | 73/81 |
| 4,007,632 | 2/1977 | Segars | 73/78 |
| 4,009,390 | 2/1977 | Satterlee et al. | 378/45 |
| 4,939,927 | 7/1990 | Johnston | 73/81 |

OTHER PUBLICATIONS

Watanabe et al. Jpn J. Zootech Sci., vol. 51 (12), pp. 845–851. (AN 81: 236543, Biosis), 1980.

S.P. Timoshenko and J.N. Goodier, "Theory of Elasticity," Third Edition, McGraw–Hill, Inc., Copyright 1970 by the United Engineering Trustees, Inc.

Dissertation by Maria Victoria Spadaro, "Biochemical Characterization of Meat Texture," Aug. 1996.

*Primary Examiner*—Maureen M. Wallenhorst
*Attorney, Agent, or Firm*—Baker & Botts, L.L.P.

[57] ABSTRACT

A method for estimating the tenderness of a meat product is provided. The method includes determining the stress relaxation coefficient of a meat sample. One or more physical parameters of the meat sample are then determined from the stress relaxation coefficient. Diagnostic sensory characterization data, such as a numerical estimation of the meat's overall tenderness, is then determined for the meat sample. The physical parameters are then correlated to the diagnostic sensory characterization data, to allow the diagnostic sensory characterization data to be estimated solely from the measured physical parameters.

13 Claims, 2 Drawing Sheets

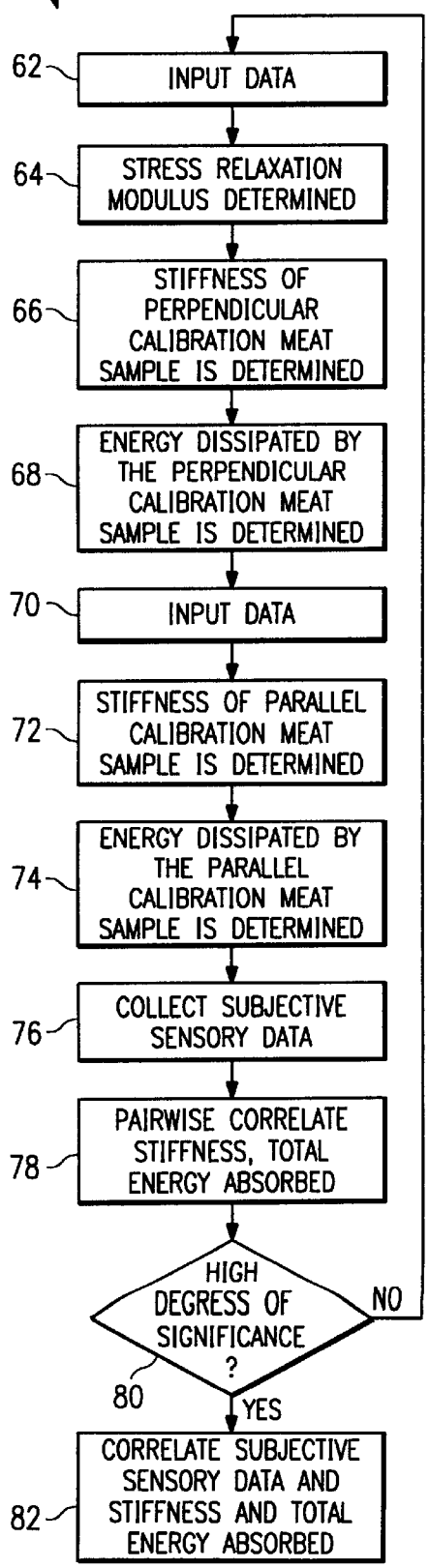
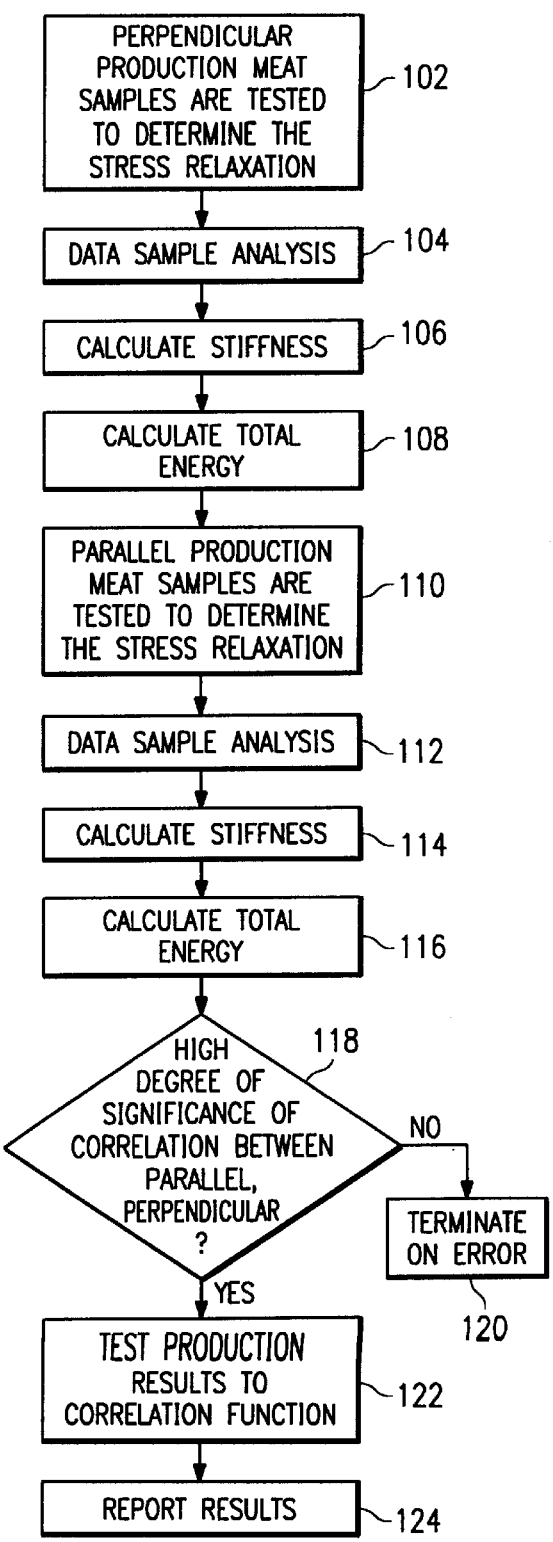

METHOD AND SYSTEM FOR ESTIMATING THE TENDERNESS OF A MEAT PRODUCT

RELATED APPLICATIONS

This application claims the benefit of U.S. Provisional Patent Application No. 60/020,715; "Biomechanical Characterization of Meat Texture," filed Jun. 25, 1996, commonly owned and assigned with the present application.

TECHNICAL FIELD OF THE INVENTION

This invention relates generally to the field of meat processing, and more particularly to a method and system for estimating the tenderness of a meat product.

BACKGROUND OF THE INVENTION

Processing of meat for human consumption includes the characterization of meat tenderness, which is performed for the purpose of grading the meat. Tenderness may be characterized by assessing parameters that affect sensory properties, such as toughness, juiciness, firmness, mealiness, stringiness, chewiness, hardness, softness. These parameters are typically assessed subjectively, such as by having a panel of human subjects taste the meat and perform a diagnostic sensory analysis of the meat.

While diagnostic sensory characterization is acceptable, it is nevertheless problematic because the meat samples must be prepared and human subjects must test a large number of samples. Mechanized methods of estimating meat tenderness may be used instead of diagnostic sensory characterization.

One mechanized method of meat characterization is the Warner-Bratzler shear press, which measures the shear force required to cut a meat sample. Although this method is more convenient than diagnostic sensory characterization, the correlation between diagnostic sensory characterization and the Warner-Bratzler shear force measurements is typically low, ranging from 40 percent to 60 percent.

Because of the difficulty and cost associated with diagnostic sensory characterization, and the low correlation between known mechanized methods of estimating and diagnostic sensory characterization, these methods are not used. Instead, the predominant standard method for grading meat is the United States Department of Agriculture beef quality grading system, which is a subjective evaluation that ranks beef according to the amount of marbling and the maturity of the animal. Other methods are not used because of the prohibitive costs of such methods or the low accuracy of such methods.

SUMMARY OF THE INVENTION

Therefore, a need has arisen for an improved method and system for the characterization of meat tenderness that is repeatable, efficient, and that accurately correlates to diagnostic sensory characterizations of texture.

According to the teachings of the present invention, a method and system for estimating the tenderness of a meat product is provided that substantially eliminates or reduces disadvantages associated with prior systems and methods.

One aspect of the present invention is a method for estimating the tenderness of a meat product that includes determining the stress relaxation coefficients of a meat sample. One or more physical parameters of the meat sample are then determined from the stress relaxation coefficients. Diagnostic sensory characterizations, such as a numerical estimation of the meat's overall tenderness, are then determined for the meat sample. The physical parameters are then correlated to the diagnostic sensory characterization, to allow the diagnostic sensory data to be estimated from the physical parameters.

The present invention provides many important technical advantages. One important technical advantage of the present invention is a method for biomechanically characterizing the texture of meat that provides a better correlation with diagnostic sensory characterization than existing methods.

Another important technical advantage of the present invention is a system for biomechanically characterizing the texture of meat that measures data, converts the data into biomechanical characterizations, and outputs the biomechanical characterizations that may be correlated with diagnostic sensory characterizations.

Another important technical advantage of the present invention is a system for biomechanical characterization of meat texture that may be used to perform quick and effective testing of meat samples in convenient locations.

BRIEF DESCRIPTION OF THE DRAWINGS:

For a more complete understanding of the present invention and advantages thereof, reference is now made to the following description taken in conjunction with the accompanying drawings, in which like reference numbers indicate like features and wherein:

FIG. 3 is an exemplary method for correlating the biomechanical characterization of meat texture to diagnostic sensory characterization data in accordance with the teachings of the present invention; and FIG. 4 is an exemplary method for testing meat samples in accordance with teachings of the present invention.

DETAILED DESCRIPTION OF THE DRAWINGS:

Preferred embodiments of the present invention are illustrated in the FIGURES, like numerals being used to refer to like and corresponding parts of various drawings.

Figure 1:
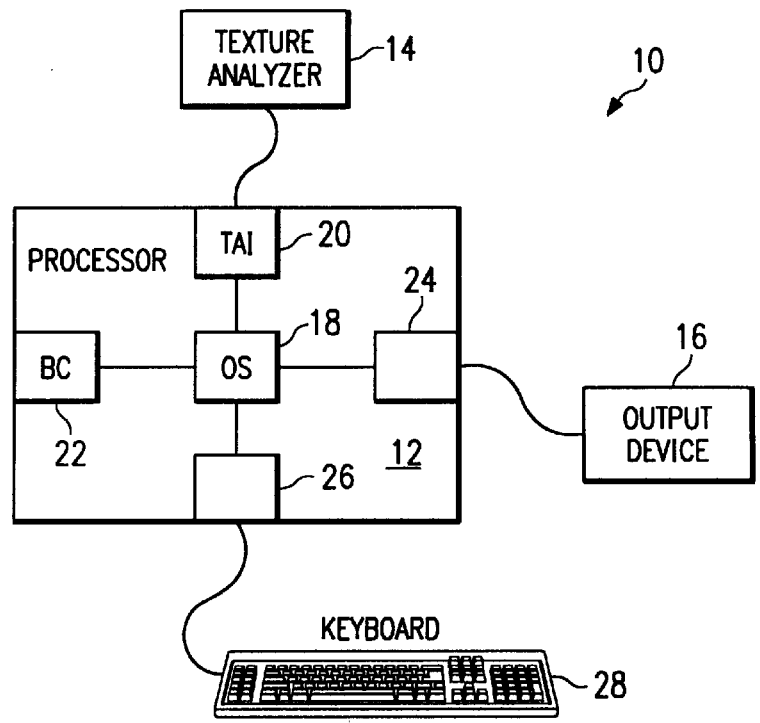
FIG. 1 is an exemplary system for estimating the tenderness of a meat product embodying concepts of the present invention.

FIG. 1 is an exemplary system 10 for estimating the tenderness of a meat product embodying concepts of the present invention. System 10 comprises processor 12, texture analyzer 14, and output device 16. Texture analyzer 14 performs physical tests on samples of meat, generates electrical signals in response to those tests, and transmits the signals to processor 12. Software operating on processor 12 performs an analysis of data derived from the electrical signals received from texture analyzer 14. Output device 16 receives data from processor 12 and generates visual and graphical data.

Processor 12 comprises programmable data processing equipment that may include a microprocessor, a random access memory (RAM), a disk driver, input/output devices, network interface cards, printer cards, sound cards, CD-Rom drive interface cards, and other typical programmable data processing equipment components. Processor 12 may comprise other suitable processors that are operable to implement operating system (OS) 18, texture analyzer interface system (TAI) 20, biomechanical characterization system (BC) 22, and output interface system 24, including but not limited to a, personal computer, a laptop computer, a programmable controller, and a workstation.

Operating system 18 comprises a processor operating system that performs general processor operating functions, such as memory management, file management, and the transmission of data between systems and peripheral devices. Operating system 18 is a commercially-available operating system, such as MICROSOFT DOS or MICROSOFT WINDOWS, but may alternatively comprise an optimized operating system for use with texture analyzer interface system 20, biomechanical characterization system 22, and output interface system 24.

Texture analyzer interface system 20 comprises circuitry and software that are operable to receive transmitted data from a first medium, to convert the transmitted data from a first format to a second format, and to transmit the data over a second medium. Texture analyzer interface system 20 is coupled to operating system 18 and texture analyzer 14, and transfers data between operating system 18 and texture analyzer 14. Texture analyzer interface system 20 may comprise commercially available circuitry and software that are operable to interface with texture analyzer 14 and operating system 18.

Biomechanical characterization system 22 comprises circuitry and software that are operable to receive data from texture analyzer interface system 20 and to process the data. Biomechanical characterization system 22 is coupled to texture analyzer interface system 20 and output interface system 24 via operating system 18.

Biomechanical characterization system 22 receives data that is representative of the force applied to meat samples as a function of time. Biomechanical characterization system 22 is operable to determine the stiffness and total dissipated energy of the meat samples from the change of applied force over time.

Biomechanical characterization system 22 is further operable to receive diagnostic sensory characterization data for other meat samples, and to correlate the stiffness and total dissipated energy data with the diagnostic sensory characterization data for the meat samples.

Alternatively, or in addition, biomechanical characterization system 22 may receive the representative data of force applied to meat samples as a function of time, and may predict diagnostic sensory characterization data values for the meat samples based upon a previously determined correlation function. This correlation function may be determined from meat samples by biomechanical characterization system 22, or may be provided from an external source to biomechanical characterization system 22.

Biomechanical characterization system 22 is also operable to transmit report data to output device 16. For example, biomechanical characterization system 22 may transmit data such as the sample compressive modulus, sample stiffness, sample total energy dissipated, diagnostic sensory characterization data, or predicted diagnostic sensory characterization data for a sample to operating system 18 for output on output device 16.

Output interface system 24 comprises circuitry and software that are operable to transfer data to an output device, such as output device 16. Output interface system 24 is coupled to operating system 18 and output device 16. Output interface system 24 may comprise one or more software applications, data buses, data storage devices, and other suitable components.

Texture analyzer 14 comprises a device that performs compressive or tensile testing on a meat sample. For example, texture analyzer 14 may be a TA.XT2 Texture Analyzer (Texture Technologies Corp., Scarsdale, N.Y./ Stable Micro Systems, Godalming, UK), or may be other suitable compressive or tensile test equipment. Texture analyzer 14 is operable to apply a force to a sample, to measure the change in force over time, to measure the change in sample size over time, to generate measurement data in a predetermined format that is representative of the change in force over time, and to transfer the measurement data to texture analyzer interface system 20.

Output device 16 comprises a data output device such as a video display, a printer, a disk drive, or other suitable output device. Output device 16 is coupled to output interface system 24, and is operable to receive data from output interface system 24 and to present or store the data.

Input interface system 26 comprises circuitry and software that are operable to transfer data between an external input device and operating system 18. Input interface system 26 is coupled to operating system 18 and to keyboard 28. Input interface system 26 is operable to receive data generated by or transmitted from keyboard 28, to change the data into a format that is compatible with operating system 18, and to transmit the data to operating system 18.

Keyboard 28 comprises a keyboard data input device that is operable to generate data representative of selected keys. Keyboard 28 may alternatively comprise other suitable data input devices, including but not limited to tape drives, disk drives, ethernet interfaces, or mouse devices. Keyboard 28 is coupled to input interface system 26.

In operation, system 10 is used to correlate mechanical test results from meat samples with diagnostic sensory characterization data, and to predict diagnostic sensory characterization data from mechanical test results of meat samples. To correlate mechanical test results with diagnostic sensory characterization data, a meat sample is placed in texture analyzer 14, which subjects the meat sample to a compressive force and measures the change in force over time and the change in sample size over time. Texture analyzer 14 outputs data that characterizes the change in force and the change is sample size over time to biomechanical characterization system 22 via texture analyzer interface system 20 and operating system 18.

Biomechanical characterization system 22 converts the data for the change in force and the change in size over time into data that is representative of sample stiffness, total energy dissipated, or other suitable data that may be used for biomechanical characterization. The sample stiffness data and total energy dissipated data are then correlated with diagnostic sensory characterization data for the meat samples. This diagnostic sensory characterization data is provided to biomechanical characterization system 22 through an input device, such as keyboard 28.

After the sample stiffness data and total energy dissipated data have been correlated to the diagnostic sensory characterization data, a correlation function is generated. The correlation function may then be stored on a memory device of processor 12, or output through output interface system 24.

To predict diagnostic sensory characterization data from mechanical test results of meat samples, a meat sample is placed in texture analyzer 14, which subjects the meat sample to a compressive force and measures the change in force over time and the change in sample size over time. Texture analyzer 14 outputs data that characterizes the change in force and change in size over time to biomechanical characterization system 22 via texture analyzer interface system 20 and operating system 18.

Biomechanical characterization system 22 converts the data for change in force and change in size over time into data representative of sample stiffness and total energy dissipated, or other suitable biomechanical characterization values. The sample stiffness data and total energy dissipated data are analyzed with the correlation function, which is either retrieved from a memory device of processor 12, or which is received from input interface system 26.

The correlation function is used to generate an estimate of diagnostic sensory characterization data based upon the sample stiffness data and total energy dissipated data. For example, the correlation function may be a linear function, with values of stiffness or total energy dissipated corresponding to numerical values for diagnostic sensory characterization data as multiplied by a scaling factor. The diagnostic sensory characterization data may then be stored on a memory device of processor 12, or output to an output device 16 through output interface system 24.

Figure 2:
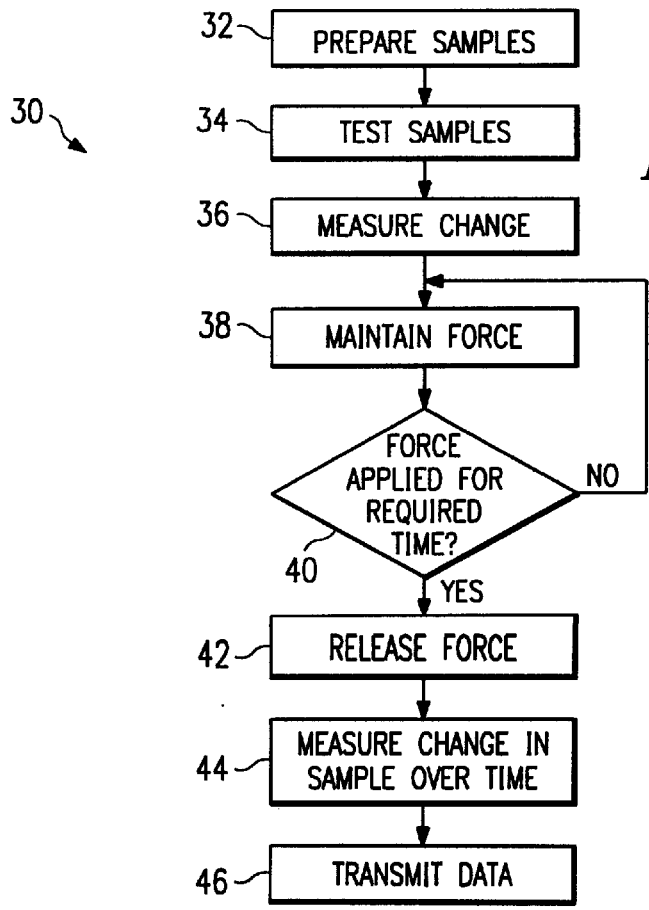
FIG. 2 is an exemplary method for estimating the tenderness of a meat product in accordance with the teachings of the present invention.

FIG. 2 is an exemplary method 30 for generating biomechanical data for meat samples in accordance with the teachings of the present invention. Method 30 may be used to generate biomechanical data for meat samples for correlation with diagnostic sensory characterization data, and may be implemented in conjunction with a system for estimating the tenderness of a meat product, such as system 10 of FIG. 1.

At step 32, meat samples are prepared from a meat specimen. For example, Longissimus Dorsi muscles may be prepared as meat samples by tempering to 5° C. for a predetermined period of time. When the temperature of the Longissimus Dorsi muscles is homogeneous, the meat samples may then be prepared by cutting the muscle perpendicular to the myofiber direction into cubes of thirty millimeters side length. The temperature of the cubes may then be allowed to equilibrate to room temperature (21°±20° C.).

Each individual cube may then be fixed on parallel faces with cyanoacrylate (super glue) to self-adhesive medium sand paper. Other sampling methods may also be used, such as in-situ sampling for meat samples, that do not require the steps of cutting the samples to a predetermined size and adhering the meat sample with cyanoacrylate to self adhesive medium sand paper.

At step 34, a force is be applied to the meat sample in either a compressive or a tensile direction. For example, the sample may be set onto a platform of a TA.XT2 Texture Analyzer (Texture Technologies Corp., Scarsdale, N.Y./ Stable Micro Systems, Godalming, UK) with its crosshead in contact with the upper face of the sample. A compressive force of constant strain may then be applied to the meat sample.

At step 36, the change in size of the meat sample is measured. For example, meat sample size may be measured in terms of percent change. As a compressive force is applied to the meat sample, the sample will become increasingly smaller, such that the sample size progresses from 99% to 98% to 97%, etc. of its original size.

At step 38, the amount of force necessary to obtain the desired change in the meat sample size is applied. For example, if a meat sample size of 97% is desired, corresponding to a 3% compressive strain level, the amount of force necessary to maintain the 3% compressive strain level is maintained at step 38.

At step 40, it is determined whether the force has been applied for the required amount of time. For example, a typical test for biomechanical characterization of meat texture may require the application of force for four minutes. After the required amount of time has elapsed, the method proceeds to step 42. Otherwise, the method returns to step 38. At step 42, the force being applied to the meat sample is released.

At step 44, the change in size of the meat sample is measured over time. For example, the change in size may be measured at a speed of 50 points per second, such that 50 data points are measured every second. At step 46, the data points measured in steps 36 and 44 are transmitted to a biomechanical characterization system such as biomechanical characterization system 22.

FIG. 3 is an exemplary method 60 for simulating the masticatory process in accordance with concepts of the present invention. Method 60 may be implemented with a biomechanical characterization system such as biomechanical characterization system 22 of FIG. 1.

Steps 62 through 74 describe an exemplary method for first converting input data for measured change in force and size of meat samples over time into suitable physical parameters by using stress relaxation coefficients for the meat samples. These physical parameters may then be correlated with diagnostic sensory characterization data in accordance with steps 76 through 82. Method 60 begins at step 62, where input data is provided to a biomechanical characterization system. This data may include a number of points that describe the change in a sample size as a function of applied force over a period of time. This input data is taken for a meat sample oriented perpendicular to the myofiber direction ("perpendicular meat sample").

At step 64, the stress relaxation coefficients for an equation that describes the stress relaxation modulus are determined from the input data for the perpendicular meat sample. For example, a three term prony series plus an infinite equilibrium term function may be used to fit the input data to the following function that describes the stress relaxation modulus:

$$E(t) = c_1 e^{-c_2 t} + c_3 e^{-c_4 t} + c_5 e^{-c_6 t} + c_7$$

At step 66, the stiffness of the perpendicular meat sample is determined by solving the following functions:

$$\sigma_{ij} = \int_0^t E_{ijkl}(t-\tau) d\frac{\epsilon_{kl}}{d\tau} d\tau$$

$$\epsilon_{ij} = \int_0^t D_{ijkl}(t-\tau) d\frac{\sigma'_{kl}}{d\tau} d\tau$$

Since the boundary regions of the material are time independent and variables are proportional in time, the solution may be reduced to the following equations:

$$\epsilon_{ij}(x_k,t) = \epsilon_{ij}{}^0(x_k) M(t)$$

$$\sigma_{ij}(x_k,t) = \sigma_{ij}{}^0(x_k) F(t)$$

A Boussinesq solution may be applied to this problem, where:

$$\sigma^o_{rr} = \frac{2P\cos\theta}{\pi \quad r}$$

The initial and final stiffness K may be calculated as:

$$K(t) = \frac{\overline{\sigma_{22}}}{\overline{\epsilon_{22}}}$$

where σ equals the stress coefficient and ε equals the strain coefficient.

At step 68, the energy dissipated by the perpendicular meat sample is determined in accordance with the following function:

$$E_D = \int_0^t \int_0^t D_{ijkl}(t-\tau)d\frac{\sigma_{kl}}{d\tau}d\frac{\sigma_{ij}}{d\tau}d\tau d\eta$$

At step 70, input data is provided to the biomechanical characterization system for a meat sample oriented parallel to the myofiber direction ("parallel meat sample"). At step 72, the values of initial and final stiffness are determined for the parallel meat sample in accordance with the equations discussed at step 66. Likewise, at step 74, the energy dissipated by the meat for the parallel meat sample in accordance with the equations discussed at step 68.

At step 76, perpendicular and parallel meat samples are provided to human tasters to collect diagnostic sensory characterization data, such as overall tenderness, fiber tenderness, juiciness, or other similar diagnostic sensory characterization data. The human tasters are typically a statistically relevant group of trained individuals that are capable of providing a numerical grade for diagnostic sensory characterization data relative to other foodstuffs, such as cheese. The diagnostic sensory characterization data obtained from individual tasters typically correlates with the diagnostic sensory characterization data for other individual tasters, where the correlation is significant to a high degree of relevance.

At step 78, the initial and final stiffness and total energy data for the perpendicular and parallel meat samples are pairwise correlated. For example, test results indicate that the correlation between initial and final stiffness for the parallel meat sample and initial and final stiffness for the perpendicular meat samples, respectively, were significant to a high degree of relevance.

Correlation to a high degree of relevance was also found between initial and final stiffness values for parallel and perpendicular meat samples, respectively. The correlation between total energy dissipated for the parallel and perpendicular meat samples has also been found to be significant to a high degree of relevance.

At step 80, it is determined whether a high degree of relevance was found for the pairwise correlation of stiffness and total energy dissipated. If a high degree of relevance is found at step 80, the method proceeds to step 82, where correlation between diagnostic sensory characterization data and stiffness and total energy dissipated is determined. For example, it has been found for certain meat samples that the best correlation between measured data and diagnostic sensory characterization data occurs when the measured data is the total energy dissipated in a parallel meat sample.

If a high degree of relevance is not found at step 80, the method returns to step 62 for compilation of a new data set. In addition, the sample population and diagnostic sensory characterization data is also scrutinized to ensure that no sample contamination has occurred. The steps in method 60 may also be performed by using mean values for a statistically significant number of meat samples. This can be accomplished by first determining a mean value of one or more physical parameters for the number of meat samples from the stress relaxation coefficients of each meat sample, and then determining a mean value of the diagnostic sensory characterization data obtained for the number of meat samples tasted. These mean values are correlated in accordance with the procedures described in steps 78–82.

FIG. 4 is an exemplary method 100 for testing meat samples in accordance with teachings of the present invention. Method 100 begins at step 102, where perpendicular meat samples are tested to determine the stress relaxation coefficients. At step 104, the data for the perpendicular production samples are transmitted to a biomechanical characterization system such as biomechanical characterization system 22 of FIG. 1.

At step 106, the stiffness values for the perpendicular production samples are calculated, such as by using the equations of step 66 of method 60. At step 108, the total energy of the perpendicular production samples is calculated, such as by using the equations of step 68 of method 60. The method then proceeds to step 110.

At step 110, parallel meat samples are tested to determine the stress relaxation coefficients. At step 112, the data for the parallel production samples are transmitted to the biomechanical characterization system.

At step 114, the stiffness values for the perpendicular production samples are calculated, such as by using the equations of step 66 of method 60. At step 116, the total energy of the perpendicular production samples is calculated, such as by using the equations of step 68 of method 60. The method then proceeds to step 118.

At step 118, the degree of relevance of the correlation between the parallel production samples and the perpendicular production samples is tested. If a high degree of relevance is not found, then the method terminates on an error signal at step 120. Otherwise, the method proceeds to step 122, where the production results are tested to the correlation function obtained from the calibration tests.

At step 124, the results of the comparison of the production results to the correlation function are reported, such as by printing a report at output device 16 of FIG. 1. The method then terminates.

In operation, meat samples are tested to determine the stress relaxation coefficients that define the stress relaxation as a function of time, such as by measuring displacement per applied force at a plurality of data points as a function of time. This data is then used to determine the initial and final stiffness and total energy dissipated by the meat samples. The data is tested for correlation between initial and final stiffness and for total energy dissipated.

Additional meat samples are then tested by human taste testers for diagnostic sensory characterization data. This diagnostic sensory characterization data is then tested for correlation to the stiffness and total energy dissipated data, and a correlation function is determined. For example, it has been found that there is a strong correlation between total tenderness and total energy dissipated for some types of meat samples.

This correlation function is then used to predict the diagnostic sensory characterization data for meat samples. The meat samples are first tested to determine the initial and final stiffness and total energy dissipated. The test data is then analyzed to determine whether there is a correlation between the physical parameters and the diagnostic sensory characterization data, and whether this correlation is significant to a high degree of relevance. If previously observed degrees of relevance are not found, then the test is aborted and the source of error is determined. Otherwise, the results of the production tests are then analyzed in accordance with the correlation function to predict the diagnostic sensory characterization data for the meat samples.

The present invention provides many important technical advantages. One important technical advantage of the present invention is a method for biomechanically characterizing the texture of meat that provides a better correlation with diagnostic sensory characterization data than existing methods. Another important technical advantage of the present invention is a system for biomechanically characterizing the texture of meat that measures data, converts the data into biomechanical characterizations, and outputs the biomechanical characterizations for correlation with diagnostic sensory characterization data. Yet another important technical advantage of the present invention is a system for biomechanical characterization of meat texture that may be used to perform quick and effective testing of meat samples in convenient locations.

Although the present invention has been described in detail, it should be understood the various changes, substitutions, and alterations can be made hereto without departing from the spirit and scope of the invention as defined by the appended claims.

What is claimed is:

1. A method for measuring the tenderness of a meat product comprising:
    determining stress relaxation coefficients of a sample of the meat product;
    determining one or more physical parameters from the stress relaxation coefficients;
    retrieving diagnostic sensory characterization data of the sample that reflect the tenderness of the sample;
    quantifying the diagnostic sensory characterization data;
    correlating the one or more physical parameters to the diagnostic sensory characterization data to verify that the physical parameters reflect the tenderness of the meat product; and
    wherein determining one or more physical parameters comprises determining a total energy dissipated in the sample.

2. The method of claim 1 further comprising:
    determining a correlation function for the meat product from the correlation between the one or more physical parameters and the diagnostic sensory characterization data of the sample; and
    using the correlation function to estimate diagnostic sensory characterization data for the meat product.

3. The method of claim 1 further comprising:
    determining a correlation function for the meat product from the correlation between the one or more physical parameters and the diagnostic sensory characterization data;
    determining stress relaxation coefficients of a plurality of samples of the meat product;
    determining one or more physical parameters of each of the samples from the stress relaxation coefficients; and
    using the correlation function to estimate product diagnostic sensory characterization data for the meat product, based upon the one or more physical parameters determined for each of the samples.

4. The method of claim 1 wherein determining one or more physical parameters comprises determining an initial stiffness of the sample.

5. The method of claim 1 wherein determining one or more physical parameters comprises determining a final stiffness of the sample.

6. The method of claim 1 wherein determining the stress relaxation coefficients of the sample comprises:
    applying a force to the sample;
    measuring a displacement over time of the sample in the direction of the applied force; and
    using the measured displacement over time of the sample to determine the stress relaxation coefficients of the sample.

7. The method of claim 6 wherein the force causes the sample to compress to 97 percent of its original size.

8. The method of claim 1 wherein correlating the one or more physical parameters to the diagnostic sensory characterization data further comprises:
    determining stress relaxation coefficients of each of a statistically significant number of samples of the meat product;
    determining a mean value of one or more physical parameters for the statistically significant number of samples from the stress relaxation coefficients of each sample;
    retrieving diagnostic sensory characterization data for the statistically significant number of samples;
    quantifying the diagnostic sensory characterization data;
    determining a mean value of the quantified diagnostic sensory characterization data for the statistically significant number of samples; and
    correlating the mean value of the one or more physical parameters to the mean value of the diagnostic sensory characterization data.

9. A method for measuring the tenderness of a meat product comprising:
    determining stress relaxation coefficients of a sample of the meat product;
    determining one or more physical parameters from the stress relaxation coefficients;
    retrieving diagnostic sensory characterization data of the sample that reflect the tenderness of the sample;
    quantifying the diagnostic sensory characterization data;
    correlating the one or more physical parameters to the diagnostic sensory characterization data to verify that the physical parameters reflect the tenderness of the meat product; and
    correlating a first physical parameter with a second physical parameter to verify that the physical parameters have been properly derived from the stress relaxation coefficients.

10. The method of claim 9 wherein the first physical parameter is based on a measurement of stress relaxation coefficients parallel to a myofiber direction of the sample, and the second physical parameter is based on a measurement of stress relaxation coefficients perpendicular to a myofiber direction of the sample.

11. A method for estimating diagnostic sensory characterization data for a meat product comprising:
    determining stress relaxation coefficients of a meat sample of a meat product;
    determining one or more physical parameters of the meat sample from the stress relaxation coefficients;
    using a correlation function to estimate diagnostic sensory characterization data for the meat product based upon the one or more physical parameters determined for the meat sample; and
    wherein the one or more physical parameters is a total dissipated energy of the meat sample.

12. The method of claim 11 wherein the step of using a correlation function comprises:

retrieving a correlation function determined from samples not taken from the meat product being tested; and using the correlation function to estimate diagnostic sensory characterization data for the meat product, based upon the one or more physical parameters determined for the meat sample.

13. The method of claim 11 wherein the correlation function is determined from samples taken from the meat product being tested.

* * * * *

UNITED STATES PATENT AND TRADEMARK OFFICE
CERTIFICATE OF CORRECTION

PATENT NO. : 6,001,655
DATED : December 14, 1999
INVENTOR(S) : Spadaro et al.

It is certified that error appears in the above-identified patent and that said Letters Patent is hereby corrected as shown below:

Col. 5, line 38, after "temperature", delete "(21°±20°C)" and insert --(21°±2°C)--.

Col. 10, line 63, after "product", insert --,--.

Signed and Sealed this

Ninth Day of January, 2001

Attest:

Q. TODD DICKINSON

Attesting Officer      Commissioner of Patents and Trademarks